United States Patent [19]

Lodder

[11] Patent Number: 5,124,932

[45] Date of Patent: * Jun. 23, 1992

[54] METHOD FOR ANALYZING ASYMMETRIC CLUSTERS IN SPECTRAL ANALYSIS

[75] Inventor: Robert A. Lodder, Lexington, Ky.

[73] Assignee: Indiana University Foundation, Bloomington, Ind.

[*] Notice: The portion of the term of this patent subsequent to Jan. 9, 2007 has been disclaimed.

[21] Appl. No.: 734,047

[22] Filed: Jul. 22, 1991

Related U.S. Application Data

[63] Continuation of Ser. No. 358,813, May 30, 1989, abandoned, which is a continuation-in-part of Ser. No. 166,233, Mar. 10, 1988, Pat. No. 4,893,253.

[51] Int. Cl.$^5$ .................. G06F 15/42; G06F 15/20
[52] U.S. Cl. .................. 364/498; 364/497
[58] Field of Search .................. 364/496–499, 364/413.01, 413.02, 525; 250/338.1, 338.5, 339–343; 356/36, 51, 30, 319, 328, 334

[56] References Cited

U.S. PATENT DOCUMENTS

| | | | |
|---|---|---|---|
| 4,286,327 | 8/1981 | Rosenthal et al. | 364/498 |
| 4,399,361 | 8/1983 | Zanzucchi et al. | 250/341 |
| 4,466,076 | 8/1984 | Rosenthal | 364/498 |
| 4,496,839 | 1/1985 | Bernstein et al. | 250/341 |
| 4,540,282 | 9/1985 | Landa et al. | 356/328 |
| 4,633,087 | 12/1986 | Rosenthal et al. | 250/339 |
| 4,652,756 | 3/1987 | Ryan et al. | 250/338.5 |
| 4,692,620 | 9/1987 | Rosenthal | 250/339 |
| 4,742,228 | 5/1988 | Bischoff | 356/36 |
| 4,785,184 | 11/1988 | Bien et al. | 250/339 |
| 4,893,253 | 1/1990 | Lodder | 364/497 |

OTHER PUBLICATIONS

"Detection of Subpopulations in Near-Infrared Reflectance Analysis", Lodder et al., (Nov. 1988), Applied Spectroscopy, vol. 42, No. 8; pp. 1500–1511.

R. Lodder, "Solving the False Sample Problem in Near-Infrared Reflectance Analysis", University Microfilms, 1988.

R. Lodder et al., "Detection of Capsule Tampering by Near-Infrared Reflectance Analysis", Anal. Chem., 59(15):1921–1930 (1987).

E. Ciurczak et al., "Identification of Actives in Multicomponent Pharmaceutical Dosage Forms Using Near-Infrared Reflectance Analysis", Spectroscopy, 1(1):36–39 (Jan. 1986).

D. Burns, "Letter to the Editor", Spectroscopy, 1(3):10 (Mar. 1986).

E. Ciurczak et al., "Determination of Particle Size of Pharmaceutical Raw Materials Using Near-Infrared Reflectance Spectroscopy", Spectroscopy, 1(7):36–39 (Jul. 1986).

C. Watson, "Near-Infrared Reflectance Spectrophotometric Analysis of Agricultural Products", Anal. Chem., 49(9):835A–840A (Aug. 1977).

D. L. Wetzel, "Near-Infrared Reflectance Analysis, (List continued on next page.)

Primary Examiner—Kevin J. Teska
Attorney, Agent, or Firm—Kirkland & Ellis

[57] ABSTRACT

The multiple linear regression approach typically used in near-infrared spectrometry yields equations in which any amount of reflectance at the analytical wavelengths leads to a corresponding composition value. As a result, when the sample contains a component not present in the training set, erroneous composition values can arise without any indication of error. There is described a method of detecting "false" samples by constructing a multi-dimensional form in space using reflectance values of samples in a training set at a number of wavelengths. A new sample is projected into this space and a confidence test is executed to determine whether the new sample is part of the population from which the training set was drawn. The method relies on few assumptions about the structure of the data; therefore, deviations from assumptions do not affect the results of the confidence test.

11 Claims, 7 Drawing Sheets

OTHER PUBLICATIONS

Sleeper Among Spectroscopic Techniques", Anal. Chem., 55(12):1165–1172 (1983).

B. W. Hadzija et al., "Simple Techniques to Detect and Identify Phentermine Adulteration", *Forensic Sci. Int'l*, 23:143–147 (1983).

B. Efron, "Nonparametric Estimates of Standard Error: The Jackknife, The Bootstrap and Other Methods", *Biometrika*, 68 (3):589–599 (1981).

H. L. Mark et al., "Qualitative Near-Infrared Reflectance Analysis Using Mahalanobis Distances", Anal. Chem., 57:1449–1456 (1985).

H. L. Mark, "Normalized Distances for Qualitative Near-Infrared Reflectance Analysis", Anal. Chem., 58:379–384 (1986).

D. E. Honigs et al., "Number of Samples and Wavelengths Required for the Training Set in Near-Infrared Reflectance Spectroscopy", Appl. Spectr., 38(6):844–847 (1984).

D. E. Honigs et al., "Near-Infrared Spectrophotometric Methods Development with a Limited Number of Samples: Application of Carbonate in Geological Samples", *Appl. Spectr.*, 39(6):1062–1065 (1985).

R. A. Lodder, "Quantile BEAST Attacks the False-Sample Problem in Near-Infrared Reflectance Analysis", Unpublished Manuscript.

THE TRAINING PROCESS

STEP A: Collect training sample spectra at d wavelengths. Map spectra as points in d-dimensional space.

STEP B: Create replicate, Ri, of the training set by copying training samples randomly and with replacement from the training set. (Number of samples in Ri = number in training set).

STEP C: Create a large number, m, of replicate training sets. Count these with i.   $i < m$ $i = m$

STEP D: Calculate the center of each replicate set Ri. Store these centers as the bootstrap distribution B

STEP E: Calculate the center of the replicates (the center of the centers), Cb.

FIG. 5

MEASURING INDIVIDUAL NEW SAMPLES

STEP F — Take spectrum of new sample, X, at d wavelengths. Represent spectrum as a point in d-dimensional space.

STEP G — Form hyperline between X (new sample) and Cb (replicates center).

STEP H — Form hypercylinder with radius r about the hyperline. Points in B that are also inside this hypercylinder are projected onto the hyperline and the projected distances to Cb are stored as a univariate distribution Q.

STEP I — Form skew-adjusted confidence limits from Cb and medians of training set and univariate distribution.

STEP J — Identify X based on skew-adjusted confidence limits.

FIG. 6

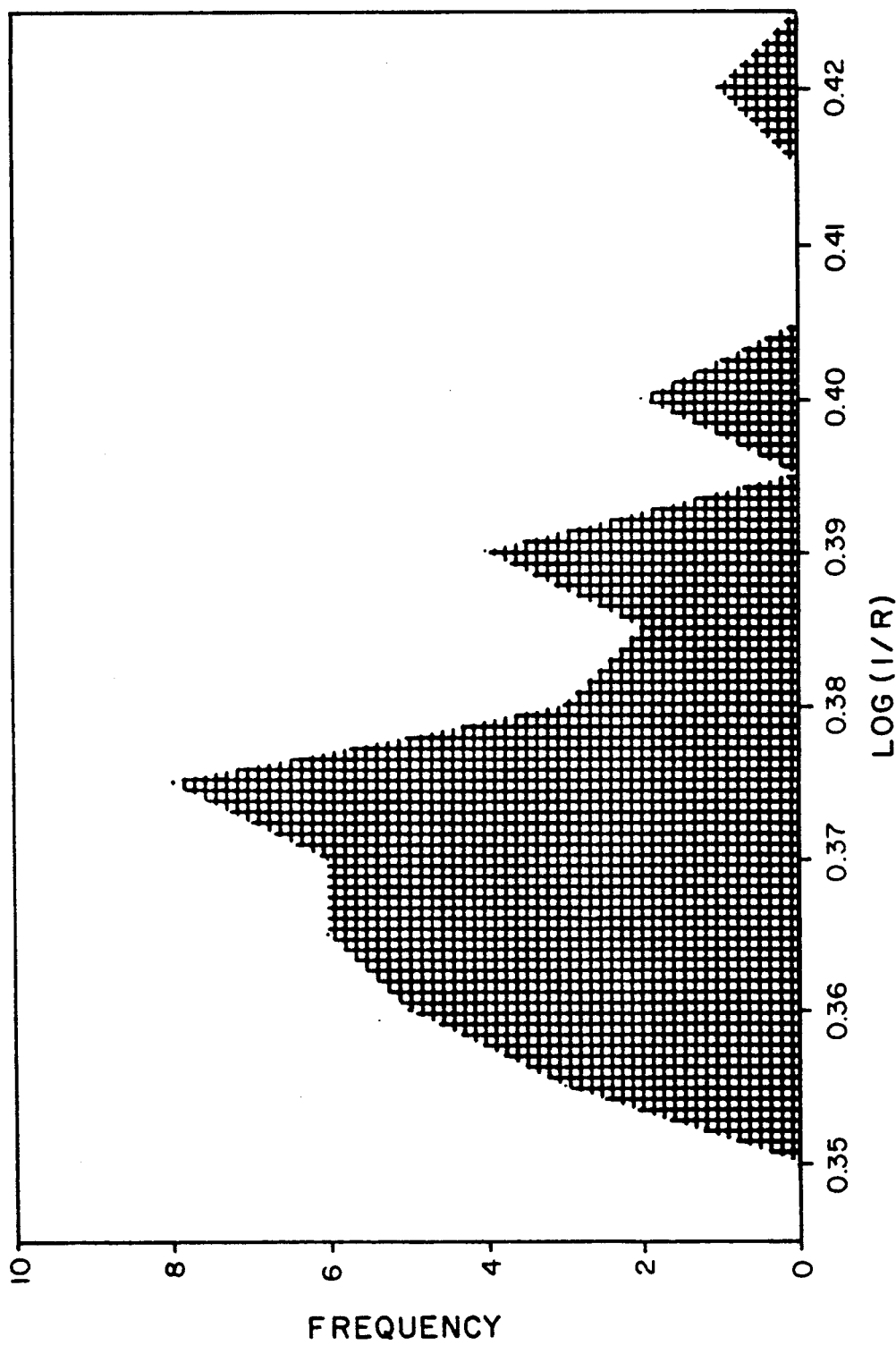

METHOD FOR ANALYZING ASYMMETRIC CLUSTERS IN SPECTRAL ANALYSIS

This is a continuation of co-pending U.S. patent application Ser. No. 07/358,813 filed on May 30, 1989, abandoned which is a continuation-in-part of U.S. Pat. Ser. No. 07/166,233 filed Mar. 10 now U.S. Pat. No. 4,893,253 issued Jan. 9, 1990.

BACKGROUND

The present invention relates to a non-invasive and non-destructive method for screening irregular or inhomogeneous samples and, in particular, for screening encapsulated drugs and tablets for contaminants and imperfections using spectral analysis and a nonparametric clustering algorithm.

The well-publicized and increasing number of cases of adulteration of non-prescription capsules has highlighted the need for rapid, non-invasive, and non-destructive methods for screening over-the-counter drugs. Near-infrared diffuse reflectance spectrometry is a fast analytical method that typically uses the reflectance of a sample at several wavelengths to determine the sample's composition. The technique is heuristic in its approach and makes extensive use of computers. Through a computational modeling process, near-infrared reflectance analysis is able to correct automatically for background and sample-matrix interferences, making ordinarily difficult analyses seem routine.

A model or calibration equation is typically a linear combination of equations of the form:

$$\text{concentration } (A) = c_o + \sum_{i=1}^{d} c_i R_i$$

where A is a sample component of interest, d is the number of wavelengths at which measurements are obtained, the $R_i$ are the sums of the sample-component signals observed at each of i wavelengths, and $c_i$ are weighting coefficients often determined by multiple linear regression. It will be appreciated that although the present application is framed in terms of near-infrared reflectance measurements, any observable, such as mass, density, magnetic behavior, radioactivity, etc., or other information may be considered a "wavelength" for use in a calibration equation.

The modeling process employs a "training set" of samples to "teach" the computer algorithm to recognize relationships between minute spectral features and the sample's composition. Of course, the training set must have been previously analyzed by some other reliable (reference) chemical procedure. Although assembling a training set and developing a new calibration can require considerable time, the speed of subsequent analysis has provided plenty of impetus for the growth of near-IR reflectance methods.

Quantitative analysis has been the principal application of near-IR reflectance analysis to date, but it can be used as a qualitative technique as well. Near-IR reflectance analysis can differentiate among a variety of pure compounds and mixtures of constant composition to solve the false-sample detection problem. A false sample is simply any sample that falls outside of the domain of the samples used to train the analysis algorithm. For example, a manufacturer might use near-IR reflectance analysis to monitor a liquid stream having a normal range of protein concentration of 3 to 6%. Training samples would be selected to completely cover this range. If a process change or equipment failure should cause the protein concentration to jump to 10%, a false-sample situation would exist. Analyzing this false sample requires extrapolating beyond the range of the training set used to generate the prediction equation. An operator should be signaled either to stop the stream an correct the equipment failure, or to recalibrate the near-IR reflectance analysis instrument to accept the new range of concentration values. This type of false-sample condition is easily detected, however, by a simple test to determine if the predicted value falls outside of the range of concentrations used in generating the prediction equation.

Another type of false-sample condition, which is more difficult to detect, arises when a new component, a component not present in the training set and therefore thoroughly unexpected, appears in the samples causing erroneous composition values to be generated. The new component could be a chemical entity, as might be introduced by opening a valve at the wrong time or by contamination of the raw materials, or a noise source, such as instrument drift over time or a change in particle-size distribution.

Detecting false samples involves the analysis of multivariate data distributions, a topic which is currently being investigated in a number of ways. Quantile analysis is a useful basis for nonparametric tests of distributional assumptions because it provides easy access to both numerical statistics and readily interpreted graphs. Quantile analysis transforms the cumulative frequency distribution of a data set into a convenient linear form from which the location, scale, and skew of data sets can be estimated. Quantile analysis provides additional advantages that are particularly useful for analyzing multivariate data as set forth in co-pending U.S. patent application Ser. No. 07/359,084, filed May 30, 1989 for Method for Detecting Subclusters in Spectral Analysis.

FIG. 1 shows two thousand simulated reflectance data points at two wavelengths for two hypothetical compounds A and B. It will be understood that each wavelength in a spectrum can be represented as a spatial dimension, giving a single point in a d-dimensional space (a hyperspace) for a spectrum recorded at d wavelengths. Thus, a 2-dimensional hyperspace is shown in FIG. 1 in general, the more dimensions provided, the more discriminating the calibration equation. The hyperspatial point is translated from the origin by amounts that correspond to the magnitude of the reflectance observed at each wavelength. By representing spectra in this manner, a group of similar samples with similar spectra appears as a cluster of points at a location in hyperspace As set forth in U.S. Pat. No. 4,893,253, a univariate distribution can be formed from the points that lie within a specified radius of a line in the hyperspace (a hyperline) such as the hyperline connecting the centers of clusters A and B, i.e., the points within the bar shown in FIG. 1.

Confidence limits are an expression of the surface of a cluster in hyperspace, i.e.. distances from the cluster center. Thus, a sample point is a member of a cluster with a given confidence or probability if the distance between the cluster center and the sample point is less than or equal to the confidence limit. The typical confidence limits that express a surface which is symmetrical through the cluster center or mean, such as a spheroid, reflect an underlying assumption of symmetry of the cluster. Such limits fail to identify accurately samples from clusters which are asymmetric.

SUMMARY

The present invention provides a method for analyzing asymmetric spectral distributions using confidence limits that are independent of the shape of the underlying sample distribution. In one aspect, the invention provides a method comprising the steps of forming a bootstrap distribution from a training set of spectra of samples drawn from a sample population, forming a univariate distribution of selected points from the bootstrap distribution, determining skew-adjusted confidence limits from the training set and bootstrap and univariate distributions, and identifying a test sample as a member of the sample population based on the skew-adjusted confidence limits.

BRIEF DESCRIPTION OF THE DRAWINGS

The objects and advantages of the invention will be more apparent after a reading of the following detailed description in conjunction with the drawings in which:

FIG. 5 shows a process for training a nonparametric clustering algorithm;

FIG. 6 shows a process for characterizing sample spectra; and

FIG. 7 shows a frequency distribution of real spectra.

DETAILED DESCRIPTION

Figure 1:
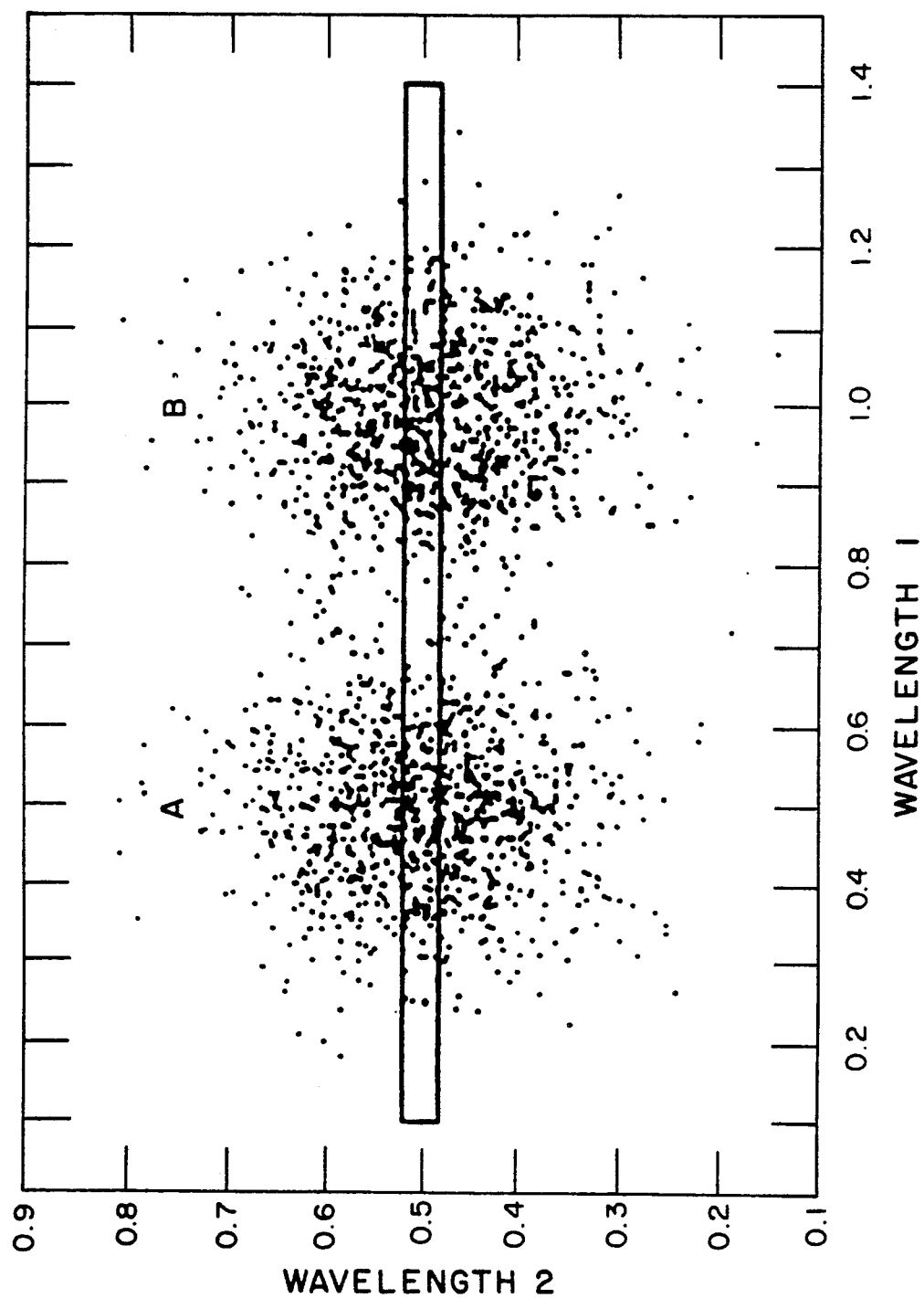
FIG. 1 shows two thousand two-wavelength spectra as points in a two-dimensional space.
Figure 2:
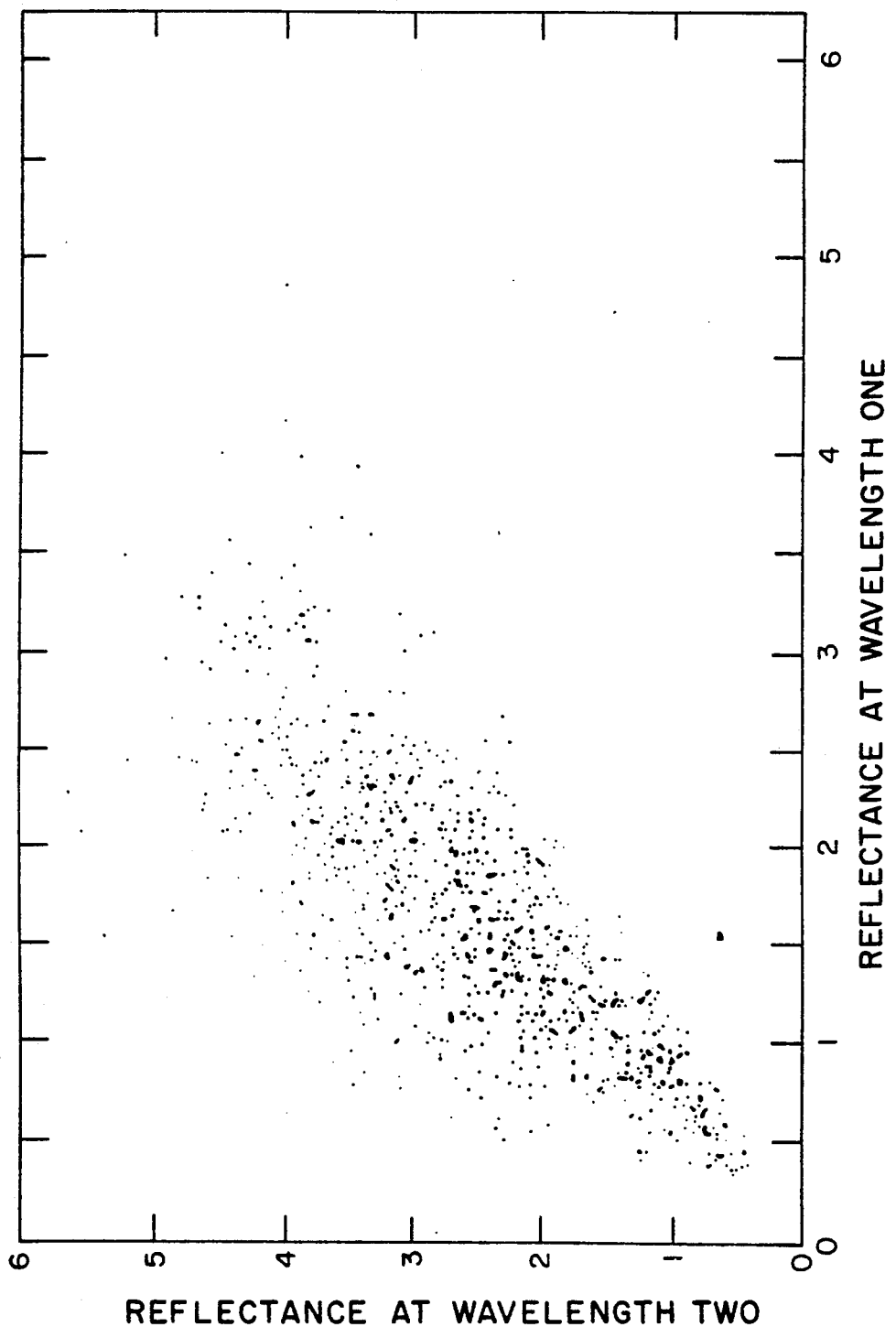
FIG. 2 shows one thousand two-wavelength spectra of three hypothetical randomly mixed compounds.
Figure 3:
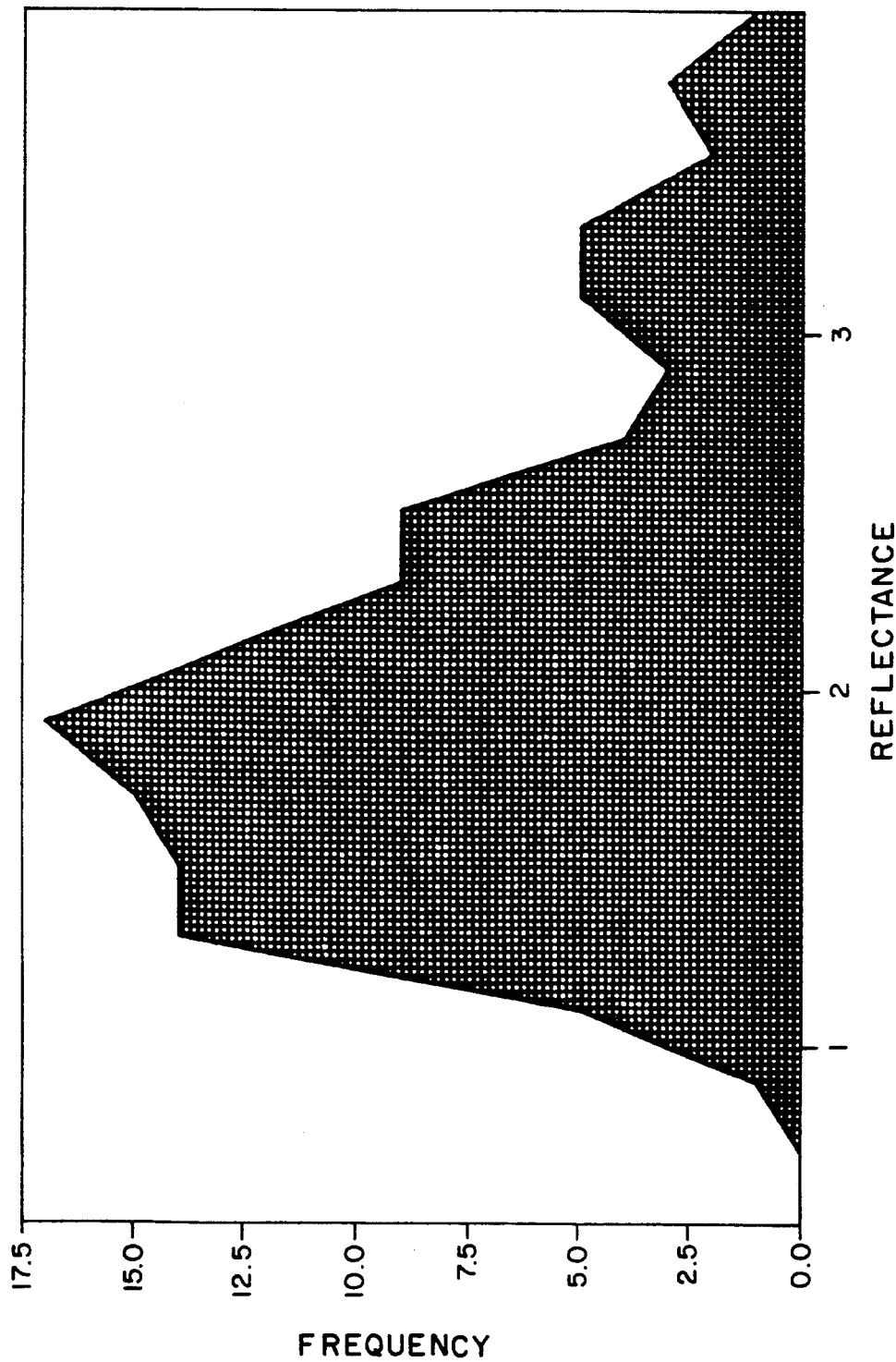
FIG. 3 shows a frequency distribution of the points inside a cylinder containing the center of the cluster of FIG. 2.

FIG. 2 shows a hyperspatial cluster formed by a training set comprising 1000 spectra of three hypothetical randomly mixed compounds A, B, and C recorded at two wavelengths. In FIG. 2, bivariate-normal noise with the variance of the horizontal axis set four times greater than that of the vertical axis has been added to the noiseless (wavelength 1, wavelength 2) reflectances of (5, 5); (5, 10); and (10, 10). The distribution of points about the center of the cluster is clearly not symmetric. A cross-section of points through the mean or center of the cluster shows a definite right (or positive) skew, indicating a leverage effect by points with higher values. (A frequency distribution polygon of such a cross-section appears in FIG. 3.) Real near-IR reflectance data also show asymmetry (see FIG. 7).

Figure 4:
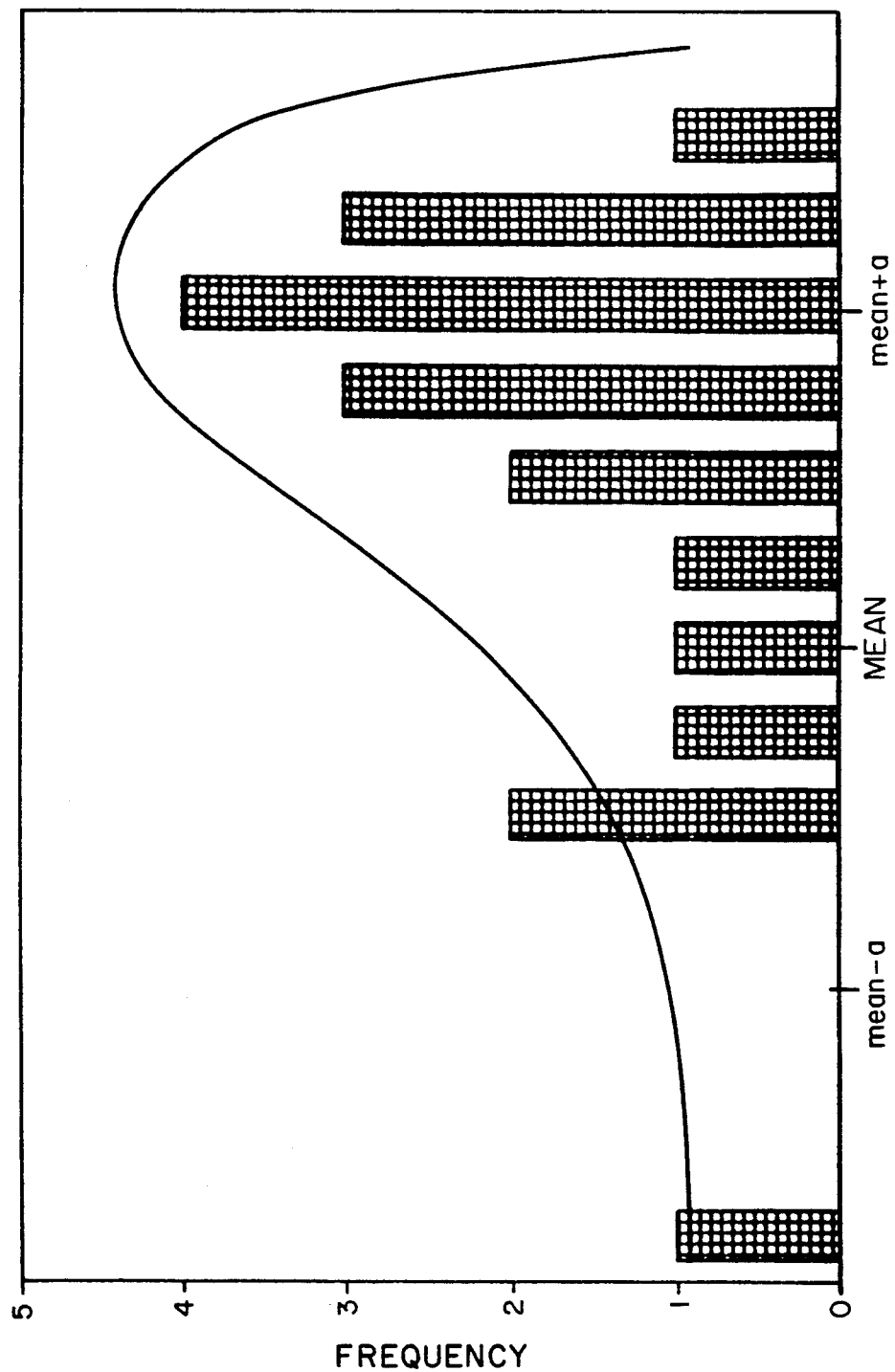
FIG. 4 shows a skewed frequency distribution of points relative to their mean.

FIG. 4 demonstrates the effect of such a skew on the determination of confidence limits. Because of the balancing property of the mean, a small number of points located some distance away from the others exert a considerable leverage on the value of the mean. When these distant points are lower values than the rest as in FIG. 4, the distribution is said to be left (or negatively) skewed, and the mean is shifted downward. In FIG. 4, the outlying points should not be discarded because the solid line represents the real underlying distribution of the total population from which the samples were drawn. For this situation, the usual symmetric statement of confidence limits, e.g.:

confidence limits for anything = mean $+/- t_{a,\psi} s$ $_{anything}$ does not provide an adequate description. See D.

G. Peters et al., "Chemical Separations and Measurements," p. 25, W. B. Saunders, Philadelphia 1974. For example, suppose the contour level of a distribution is given by $a = z_a \sigma$ (see FIG. 4) where $z_a = \Phi^{-1}(a)$ and $\Phi(a) = (2\pi)^{-\frac{1}{2}} \int_{-\infty}^{a} e^{-t^2/2} dt$. Clearly, the probability of a point appearing at mean + a is different from the probability of a point appearing at mean − a.

The BEAST (Bootstrap Error-Adjusted Single-sample Technique) is a nonparametric method (i.e., a distribution-free method whose properties hold under very few assumptions about the population from which the data are obtained) of assigning an asymmetric direction-dependent standard deviation to a multidimensional point estimate. The BEAST constructs a multi-dimensional cluster in hyperspace using the reflectances of each training-set sample at a predetermined number of wavelengths. New samples are projected into this space and a nonparametric confidence test is performed to determine whether the new sample is part of the training-set cluster. Since it is possible that the distribution underlying a set of samples is skewed, an asymmetric nonparametric method of setting confidence limits is employed in accordance with the present invention. This method does not assume that the best point estimate of the mean lies at the center of the interval between the confidence limits.

The asymmetric estimation capability is derived in part from the bootstrap, which can be summarized as follows. Given an unknown distribution function F and some parameter of interest (such as the mean or median) that is a function of a number of independent identically distributed samples from F, the bootstrap determines the standard error in the parameter of interest from the samples in a training set which is a representative sampling of the unknown distribution. The real standard error of the parameter is a function of the unknown distribution, the size of the training sample set, and the form of the parameter. Nevertheless, knowing the number of samples and the form of the parameter, the bootstrap estimate of the standard error is a function of only the unknown distribution F. In other words, although the actual distribution F is unknown, it can be estimated using the empirical probability distribution represented by the training set.

The training set, composed of a number n of equally weighted samples from the unknown distribution, is created so that the empirical probability distribution adequately describes the variation in the unknown distribution F, and remains unchanged for the remainder of the estimation procedure. In one aspect of the invention, the training set is carefully constructed from unadulterated pharmaceutical samples in a fashion that captures all possible sample variations. For example, each sample member of the training set is illuminated with near-infrared light, and its reflectance is measured at a number d of wavelengths with a suitable infrared spectrometer. The spectra are recorded and transformed or mapped to produce a set or cluster of points in hyperspace. (See FIG. 5, Step A).

Bootstrap observations are randomly and independently drawn from the training set, with replacement from the training set so that the training set is never depleted or changed, to form a bootstrap set or replicate training set with the same total number as the training set; a number m of replicate training sets are created. (See FIG. 5, Steps B and C).

The sampling distribution of the parameter of interest (e.g., the center of a group or cluster of spectral points in hyperspace) for the unknown distribution F is approximated by the multidimensional distribution of that parameter in the m bootstrap or replicate training sets (hereafter this distribution is termed simply the "bootstrap distribution"). In the present invention, the center of each replicate training set is determined by averaging the points obtained (i.e., by finding the group mean), and the centers of the replicate training sets form a bootstrap distribution B (See FIG. 5, Step D). After the bootstrap distribution B is developed from the training set, the center Cb of the bootstrap distribution is determined by averaging the centers. (See FIG. 5, Step E)

The calculation of the bootstrap distribution is preferably arrived at by a Monte Carlo approximation through which a large number (m) of bootstrap sample sets is generated by randomly drawing observations from the training set (again, with replacement from the training set) to form bootstrap sets of the same size as the training set. The empirical distribution of the corresponding values of the parameter of interest calculated using the bootstrap sets is taken as an approximation to the bootstrap distribution, and its quantiles are used to estimate the value and precision of the parameter for the original population. The Monte Carlo method is by far the most common, but not the only, method for obtaining the bootstrap distribution. Another method is direct theoretical calculation in special cases. Taylor-series expansion methods can also be used to estimate the mean and variance of the bootstrap distribution of the parameter of interest.

A training set of sample spectral values (e.g., reflectance, absorbance, etc.) recorded at d wavelengths from n training samples of a population can be represented by the n-by-d matrix T. (Generally, another n-by-d matrix V of spectra from validation samples is also assembled from the same source as the training set. The validation sample set V serves as an indicator of how well the training set describes the overall population variation.) The training set is carefully constructed from known samples (samples that have been analyzed or identified by a suitable reference procedure) that adequately describe all possible sample variations. This step is common to many spectral analysis procedures.

A predetermined number m of bootstrap replications are calculated from T, and the result is the bootstrap distribution, the m-by-d array B. The calculation can be initiated by filling a matrix P with sample numbers to be used in bootstrap sample sets $B_{(s)}$:

$$P = p_{ij} = r$$

where r is a random number between zero and unity. The values in P are scaled to the training-set size by:

$$P = [nP + 1]$$

A bootstrap sample set $B_{(s)}$ is then created for each row i of the m-by-d bootstrap distribution B by:

$$B_{(s)} = t_{Kj}$$

where K are the elements of the i-th rows of P and t are the elements of T. The q-th row of B is filled by the center of the q-th bootstrap sample set by:

$$b_{qj} = \sum_{i=1}^{n} b_{(s)ij}/n$$

and the center of the bootstrap distribution is $$c_j = \sum_{i=1}^{m} b_{ij}/m$$

The foregoing operations can then be repeated using V. Thus, a randomly selected set of samples (containing the same number of elements as the training set T) is drawn from the training set, with replacement from the training set, to form a bootstrap distribution by Monte Carlo approximation. It will be appreciated that a bootstrap distribution is used to estimate the true population distribution for a sample set.

Bootstrap distribution quantiles are readily converted into confidence intervals and are therefore useful in defining the boundaries of a training set in the hyperspace of spectral points, as described in co-pending U.S. patent application Ser. No. 07/359,084 filed May 30, 1989, incorporated herein by reference. Using the method described above in which the parameter of interest is the bootstrap-set center, selecting any two bootstrap-distribution percentiles gives the corresponding confidence limits for the center-parameter (e.g., selecting the 16th and 84th percentiles of the bootstrap distribution produces the central 68% confidence limits). This method fails to capture the asymmetry of a distribution when the median of the training set is noticeably different from the mean of the bootstrap distribution. In accordance with the present invention, a bias correction is provided in the calculation of the confidence limits that recognizes that the mean value of a distribution drifts in the direction of the skew (measured with respect to the median of the distribution). Large differences between the median and mean suggest a skew that casts doubt upon the validity of a simple symmetric confidence interval. When no difference between the mean and the median exists, the value of the correction is zero. Otherwise, new confidence limits are obtained with a improved representation of any skew present.

As described above, each monitored wavelength is considered a dimension in a hyperspace, and each point in the hyperspace represents an entire spectrum, translated from the origin by amounts that correspond to the magnitude of the reflectance observed at each wavelength. The distribution of reflectances on each wavelength axis gives projections of the clusters of points. Valid samples are defined as those that fall inside a cluster of training-set points, while false samples are those that fall outside the cluster. Confidence limits, set along any linear combination of wavelengths (dimensions), define the surface of the cluster at a specified confidence level. These confidence limits are obtained by using the bootstrap to arrive at an estimate of the real-sample population distribution based upon the training-set distribution. The center of the real-sample distribution is estimated by the center of the bootstrap-set centers (the bootstrap distribution).

When a new sample is tested, a vector or hyperline is formed in hyperspace between the new spectral point and the estimated center point of the real-sample distribution. A hypercylinder formed about this line contains a number of replicate-training-set centers. It will be appreciated that the hypercylinder is an approximation to the hyperline since hardly any replicate centers would be expected to fall on the hyperline. When the coordinates of these points are transformed into distances from the estimated center Cb of the bootstrap distribution, a univariate distribution is constructed that is used in the confidence test of the present method. The reliance on nonparametric techniques produces a false-sample test that operates without assumptions about the shape, size, symmetry, or orientation of the spectral-point cluster in hyperspace.

The spectrum X of a new sample (such as an inhomogeneous or adulterated sample) is recorded and projected as a point into the hyperspace. (See FIG. 6, Step F). A vector or hyperline is formed in hyperspace between the new hyperspatial point and the computed center point Cb of the bootstrap distribution. (See FIG. 6, Step G). A hypercylinder is formed around this hyperline (the radius r of the hypercylinder is typically 2 to 3 orders of magnitude smaller than its length) containing a number of replicate training set centers from the bootstrap distribution B (a minimum number of 50 points preferably should be used) that are projected onto the hyperline by triangulation and transformed into distances from the estimated center Cb to form a univariate distribution Q. (See FIG. 6, Step H).

The univariate distribution Q is used to construct the confidence limits. The Euclidean distances between the center Cb of the bootstrap distribution and the points in the hypercylinder are sorted, and the upper U and lower L confidence limits are scaled in accordance with a measure of the skew of Q. (See FIG. 6, Step I). The Euclidean distance from the center Cb to the new sample spectrum X is scaled by a skew-adjusted standard deviation (SD) calculated from the sorted distances. (See FIG. 6, Step J).

It will be understood that the reproducibility of the training set points may be determined by obtaining the spectra of a second or validation set of samples having the same composition as the training set and transforming the spectra obtained into points in hyperspace. If the validation set hyperspatial points fall within the cluster of the training set, the training set cluster has been validated.

The reliance on nonparametric techniques (techniques that assume no particular underlying distribution) produces an analytical method that functions without assumptions about the shape, size, symmetry or orientation of spectral-point clusters in hyperspace. This freedom is important because cluster characteristics have been shown to be unpredictable. Thus, the present method can be used both for quality control applications (i.e., to identify empty capsules, or rust, metal shavings or other contaminants in capsules) and for identification of adulterants placed in capsules (i.e., where a capsule has been the subject of deliberate tampering). Under such widely varying conditions, the unpredictability of the cluster characteristics makes the use of nonparametric techniques even more important.

The calculation of the distance between Cb and the new sample involves finding the hyperline connecting the center Cb (group mean) of the bootstrap distribution B to the new or test sample spectrum X and determining the probability of X belonging to the training set cluster T based upon the number of points (rows of the bootstrap distribution B) within a predetermined distance $r_h$ of the hyperline (in effect, taking the points or rows of B that fall within a hypercylinder of radius $r_h$). A preferable implementation proceeds toward the point-density of the hypercylinder by forming a plurality of planes connecting X, Cb, and the rows of B. The use of a plurality of planes allows a complex structure like a hypercylinder in d-dimensional hyperspace to be represented in a simple manner regardless of the number of dimensions (in fact, the number of planes is completely independent of the spatial dimension).

The 3 points that specify a plane in 3-dimensional space also specify a triangle whose sides are readily determined from:

$$S_{(02)} = \left( \sum_{j=1}^{d} (x_j - c_j)^2 \right)^{\frac{1}{2}}$$

$$s_{(OR)i} = \left( \sum_{j=1}^{d} (b_{ij} - c_j)^2 \right)^{\frac{1}{2}}$$

$$s_{(2R)i} = \left( \sum_{j=1}^{d} (b_{ij} - x_j)^2 \right)^{\frac{1}{2}}$$

where $S_{(02)}$ is the Euclidean distance from Cb to X, $s_{(OR)i}$ is the Euclidean distance from the i-th point or row of B to Cb, and $s_{(2R)i}$ is the Euclidean distance from the i-th point of B to X. (In general, a vector or array will be represented by an uppercase letter, and the vector's elements will be represented by the lowercase letter thus, it will be understood that $S_{(OR)}$ and $S_{(2R)}$ are m-element arrays.)

Once the triangles have been formed, finding the rows of B, i.e., the points of the bootstrap distribution, that fall inside the hypercylinder is now carried out by a procedure beginning:

$$s_{(UB)i} = (S_{(02)} + s_{(OR)i} + s_{(2R)i})/2$$

$$a_i = (s_{(UB)i}(s_{(UB)i} - S_{(02)})(s_{(UB)i} - s_{(OR)i})(s_{(UB)i} - s_{(2R)i}))^{\frac{1}{2}}$$

$$s_{(R)i} = 2(a_i)/S_{(02)}$$

$$s_{(p)i} = (s_{(OR)i}^2 - s_{(R)i}^2)^{\frac{1}{2}}$$

The elements of $S_{(p)}$ are Euclidean distances, from the center Cb to each point in the bootstrap distribution B, projected on the hyperline connecting Cb to the new sample spectrum X.

Constructing a hypothetical hyperplane through Cb such that the hyperline from X to Cb is normal to the hyperplane allows the $S_{(p)}$ distances to be given a direction along the hyperline. Points in the bootstrap distribution that are on the same side of the hyperplane as X are assigned positive distances in $S_{(p)}$. The remainder of the elements of $S_{(p)}$ are assigned negative values. This directional assignment is preferably accomplished by multiplying the elements $s_{(p)i}$ for which $\{S_{(02)}^2 + s_{(OR)i}^2 < s_{(2R)i}^2\}$ by $-1$.

The values of $S_{(p)}$ representing points in B that are outside the hypercylinder, i.e., those points for which $s_{(R)i} > r_h$, are discarded for the remainder of the calculations, and the other values of $S_{(p)}$ are rank-ordered, i.e.:

$$S_{(q)} = O(s_{(p)i} \text{ such that } s_{(r)i} < r_h)$$

with $n_h$ the number of elements of $S_{(q)}$, i.e., an array representation of the univariate distribution Q.

For a symmetric normal distribution, a 1-SD contour is expressed as upper U and lower L confidence limits $L = [0.16 n_h]$ and $U = [0.84 n_h]$, where the square brackets indicate the greatest integer. Thus, the symmetric confidence interval along the hyperline connecting X and Cb is: $\{s_{(q)L} < Cb < s_{(q)U}\}$. As described above, if $n_h$ is less than about 50, the interval will not be very precise. The uncorrected standard deviation $\sigma$ of the univariate distribution Q can be found by either:

$$\sigma = \frac{(|s_{(q)L}| + |s_{(q)U}|)n_h^{\frac{1}{2}}}{2}$$

or calculating the standard deviation from all of the points of $S_{(q)}$ and multiplying by $n_h^{\frac{1}{2}}$. Once $\sigma$ is known, the distance to the test spectrum in uncorrected SDs (suitable for unskewed training sets) is simply:

$$S_{(02)}/\sigma = \left(\sum_{j=1}^{d} (c_j - x_j)^2\right)^{\frac{1}{2}}/\sigma$$

Since many training sets are skewed, L and U are adjusted in accordance with the present invention to compensate for the skew before finding $s_{(q)L}$ and $s_{(q)U}$. The number m of points in the bootstrap distribution B influences the selection of an adequate contour level. For $m < 1000$ the contour should probably be one SD, so $a = \Phi(-1)$; for $m >> 1000$, e.g., $10^5$ or $10^6$, contours of two or three SDs could be used. It will be understood that as m increases $S_{((q)}$ "plateaus," or does not change, at increased contour size. Setting $z_a = \Phi^{-1}(a)$ and locating the median of the training set by $c_{(T)j} = M_j(t_{ij})$, where $t_{ij}$ denotes the i-th sample of the training set, initiates the adjustment of the confidence limits to compensate for skew.

$C_{(T)}$ tends to lie in hyperspace in the direction opposite to the direction of the skew (with respect to Cb) because of the leverage effect of skewed points on the mean. This fact is the basis of the confidence-limit adjustment in accordance with the present invention, and the calculation of the adjustment continues with a determination of the distance and direction of the difference $S_{(CP)}$ between Cb and $C_{(T)}$ projected on the hyperline connecting Cb to X:

$$S_{(COR)} = \left(\sum_{j=1}^{d} (c_{(T)j} - c_j)^2\right)^{\frac{1}{2}}$$

$$S_{(C2R)} = \left(\sum_{j=1}^{d} (c_{(T)j} - x_j)^2\right)^{\frac{1}{2}}$$

$$S_{(CUB)} = (S_{(02)} + S_{(COR)} + S_{(C2R)})/2$$

$$A_c = (S_{(CUB)}(S_{(CUB)} - S_{(02)})(S_{(CUB)} - S_{(COR)})(S_{(CUB)} - S_{(C2R)}))^{\frac{1}{2}}$$

$$S_{(CR)} = 2(A_c)/S_{(02)}$$

$$S_{(CP)} = (S_{(COR)}^2 - S_{(CR)}^2)^{\frac{1}{2}}$$

The directional sign given to $S_{(CP)}$ is opposite that given to $S_{(p)}$: if $\{S_{(02)}^2 + S_{(COR)}^2 > S_{(C2R)}^2\}$ then $S_{(CP)}$ is multiplied by $-1$.

It will be understood that if the mean and median of $S_{(q)}$ are substantially different, $S_{(q)}$ may be skewed. Since the Central Limit Theorem applies to $S_{(q)}$, a skew probably indicates that $n_h$ points are not enough to create a stable confidence-limit adjustment. If skew is present, two options are available (1) use a larger number m of replicate training sets for the bootstrap distribution B; or (2) increase $r_h$ and recalculate the univariate distribution (note that this option may cause a loss of directional selectivity that can bias the quantiles of $S_{(q)}$). Finally, it will be understood that $S_{(q)}$ is ordered so the use of some common ways of calculating $M(S_{(q)})$ will result in very poor running times for the algorithms. To efficiently find $M(S_{(q)})$, simply select the $(n_h/2 + \frac{1}{2})$th element of $S_{(q)}$ when $n_h$ is odd, and the mean of the $(n_h/2)$th and $(n_h/2 + 1)$th elements when $n_h$ is even.

In accordance with the invention, $S_{(CP)}$ is replaced by $S_{(CP)}\delta + M(S_{(q)})$ to perform well as an adjustment in a computational environment where almost any axis scale or skew is possible. The addition of $M(S_{(q)})$, the median of the univariate distribution Q, helps to assure that the correction $S_{(CP)}$ and its array-analog $z_o$ (defined below) have the same sign (direction), and the factor $\delta$ provides a skew sensitivity adjustment. Typically, $\delta$ has a value between zero and unity that is set empirically for each combination of T and B to keep the absolute magnitude of the adjustment inside the values of $S_{(q)}$.

The calculation of the $z_o$ adjustment from $S_{(CP)}$ proceeds as follows:

$$f_i = s_{(q)i} - S_{(CP)}$$

$$I_{(N)} = \{1, 2, 3, \ldots, n_h\}$$

$$z_e = [R(F(I_N))]$$

$$z_o = \Phi^{-1}[z_e/n_h]$$

where $[R(g(x))]$ denotes the greatest integer root of a function $g(x)$ found by, e.g., trapezoidal interpolation $f_i$ are the discrete samples of the distribution function F, i.e., the $n_h$ elements of $S_{(q)}$ corrected using $C_T$; and $I_{(N)}$ is a vector of $n_h$ independent variables paired with F to locate the roots of F. If $|2z_o| > |z_a|$ then $\delta$ should be decreased and the calculation redone. Otherwise, skew-corrected L and U values for $S_{(q)}$ are calculated from:

$$L_c = [\Phi(2z_o + z_a)n_h]$$

$$U_c = [\Phi(2z_o - z_a)n_h]$$

As in the case of the uncorrected SD $\sigma$, the confidence interval along the hyperline connecting X and Cb is $\{s_{(q)Lc} < Cb < s_{(q)Uc}\}$. The upper confidence limit is preferably the one closest to the test spectrum X, and the skew-adjusted standard deviation $\sigma_c$ is simply $s_{(q)Uc}$. The distance in skew-adjusted SDs from the center of the training set T to the test spectrum X is:

$$\left(\sum_{j=1}^{d} (c_j - x_j)^2\right)^{\frac{1}{2}} / ((\sigma_c/|z_a|)n_h^{\frac{1}{2}})$$

EXAMPLES

The algorithms previously described were implemented in programs using VAX-11 BASIC language (version 2.4, Digital Equipment Corporation) and SPEAKEASY IV DELTA (VMS version, Speakeasy Computing Corporation, Chicago). These programs were run on VAX-11/780 and VAX-11/785 computers. Spectral data at 18 discrete wavelengths were collected using a Technicon Instruments Corp. INFRA-ALYZER 400 filter spectrophotometer. This spectrophotometer was directly connected to a VAX-11/780 computer using custom interface and graphics programs.

Three types of demonstrations were conducted, beginning with the common compound-identification problem and proceeding to the more difficult problem of detecting contaminated mixtures. The three tests were:

1. The present method was used qualitatively to distinguish among four pure benzoic acid derivatives and aluminum oxide. Each of the compound names in Table I represents three spectra of that compound obtained by rotating the closed-sample cup in the spectrophotometer drawer and scanning through the 18 filters.

2. In the second test, a training set was composed of 40 random mixtures of salicylic, benzoic, isophthalic, and p-aminobenzoic acids. A total of 80 samples were prepared for the training set in this test: of these, 20 were retained for use in test 3 below. The proportion of each of the four benzoic acid derivative components was varied from 0 to 25% (by weight) in each sample, and the remainder was made up of aluminum-oxide as a diluent. A conventional random-mixing algorithm was used to generate the amounts to be used for each component in each sample, and each sample was examined at three wavelengths. The purpose of test 2 was to develop a large training-set spectral cluster that contained variations from a number of sources and determine whether pure samples could still be correctly identified as being different (or false) using only the training-set spectral data. The results for a few compounds from the laboratory shelf appear in Table II.

3. The 40-sample training set from test 2 was used again in conjunction with the 20 mixture samples that were held out. Ten of those 20 samples were "contaminated" with a false-sample compound to determine whether those ten samples would be flagged. The other ten were unaltered and served as validation samples.

FIG. 8 shows a frequency distribution polygon for a cross-section through the center of the training set used for Tables II and III, projected on a wavelength axis. The logarithm of the inverse reflectance value at the wavelength is on the abscissa, and the distribution is right-skewed.

The benzoic acid derivatives used in test 1 and in the training set for tests 2 and 3 were analytical reagent-grade salicylic acid, p-aminobenzoic acid, isophthalic acid, and benzoic acid. Reagent-grade aluminum oxide was used as a diluent in mixtures where a range of component concentrations was desired (tests 2 and 3). Before each sample (or sample mixture) was read in the INFRAALYZER 400 spectrophotometer, the sample was ground and mixed in a Spex mixer/mill. The powder was then sifted through a 100-mesh sieve and packed into the closed sample cup provided with the spectrophotometer. As described above, three readings were taken on each sample, each successive reading after a 120-degree rotation of the closed cup.

The ability of the present method to differentiate among four similar benzoic acid derivatives (test 1) is demonstrated by the data in Table I. The pure-compound spectra form four clusters in hyperspace whose intercluster distances (expressed in skew-adjusted standard deviations) appear in the table. The distances tabulated have units of asymmetric nonparametric central 68% confidence intervals (equivalent to one standard deviation if the underlying distribution were Gaussian) determined in accordance with the present invention. The intervals were calculated from the distance (Euclidean metric) between the 0.16 and 0.84 quantiles of the bootstrap distribution, following the projection of this distribution onto the hyperline connecting the center of the bootstrap distribution and the new-sample spectral point.

The compound heading each column was designated as the training set, so that the distance from a column-heading compound to a row-heading compound is given in terms of nonparametric standard deviations (SDs) of the column-heading compound. For example, the distance between the clusters representing benzoic acid and salicylic acid can be expressed in two ways: in terms of the standard deviation of benzoic acid in the direction of salicylic acid (39 SDs), or in terms of the standard deviation of salicylic acid in the direction of benzoic acid (137 SDs). The difference in SDs, of course, reflects the difference in the variances (sizes) of the benzoic and salicylic acid clusters in the direction of each other.

Benzoic acid exhibited the largest overall variance of any of the compounds tested because it was difficult to grind. Incompletely ground crystals could slip through a 100-mesh sieve and thereby introduce an additional source of variation into the benzoic acid data cluster. The variance in the other compounds can be attributed primarily to orientation effects caused by packing peculiarities, because this was the only factor that was varied between replicate measurements of these substances. Aluminum oxide (included in this test because it was used as the diluent in tests 2 and 3) had the smallest overall variance probably because it was the only reagent that was available in a powder fine enough to pass through the 100-mesh sieve.

Other distances in Table I ar also in accordance with what might be predicted aluminum oxide and isophthalic acid are 4208 SDs apart because chemically they have little in common. In fact, aluminum oxide is the most distinct from the other compounds Benzoic acid and salicylic acid form the closest spectral clusters since they differ by only a single oxygen atom. For the pure components, only a small number of bootstrap replications are required (m=50) because the variance of the training set spectra is relatively small, and the distance between adjacent clusters (measured in 18-dimensional space) is relatively large. This clear disparity allows the samples to be distinguished computationally in a fraction of a second. Considering the distances (in terms of SDs) involved, there would be little danger of misidentifying the pure compounds.

A large number of sample components, varying over a relatively broad range of concentrations, can have the effect of "filling" the spectral hyperspace provided by only a few analytical wavelengths. This phenomenon is demonstrated by the 3-wavelength training set used in obtaining Table II. The Euclidean distances (not shown) for the data in Tables I and II were within an order of magnitude or so of each other; however, the distances in terms of standard deviation units are far different. The reason that the distances in SDs shrink so much from Table I to Table II is that the cluster size in Table II increased by about a factor of 100. This spread causes some apparently unrelated compounds, like sucrose and whole wheat flour, to appear to be similar to the training set of benzoic acid derivatives. The increase in training-set cluster size also highlights the need to be aware of the exact shape of the training-set cluster when small distances are to be used for identifying valid or false samples. Finally, mixing a number of different components in each sample dilutes the contribution of each component to the total sample spectrum, in effect compressing the available analytical space and increasing the probability of mixture-clusters overlapping. (This behavior can be seen in FIG. 2.)

The third test of the BEAST investigated a worst-case mixture-overlap situation by employing the same training set described in test 2 to train the BEAST algorithm. The algorithm was then presented with the remaining 20 sample mixtures. Ten of these 20 mixtures were "contaminated" with acetylsalicylic acid (randomly varying over a range from 1 to 20%). The results appear in Table III. Even in this worst-case example it is apparent that the contaminated samples were likely to be detected as false. Three out of ten of the contaminated samples failed a 3-SD test, and none of the uncontaminated samples were incorrectly identified.

One might wonder why the distance (in terms of SD ) for similar contaminant concentrations varies so widely among contaminants in Table III and why contaminant concentration does not appear to correlate well to distance. When components similar to acetylsalicylic acid rise in concentration, a 1% contribution to the sample spectrum from acetylsalicylic acid becomes relatively smaller, and the sample spectral point appears to move closer to the training set. Table IV shows the distance response of the BEAST for two groups of similar acetylsalicylic acid contaminant concentrations. The concentration of the diluent (aluminum oxide) is inversely related to the concentrations of the benzoic acid derivatives, so lower diluent concentrations indicate an increase in the concentrations of the other (non-contaminant) compounds. The relative increase in the concentrations of the non-contaminant compounds, in turn, correlates to a decrease in the distance of the sample from the training set.

TABLE I

Using the BEAST for Qualitative Analysis Differentiating Among Four Benzoic-Acid Derivatives and a Diluent (distances in skew-adjusted SDS[a])

|        | Isoh2p[b] | Benzo[c] | Al2O3[d] | Salcyl[e] | PABA[f] |
|--------|-----------|----------|----------|-----------|---------|
| Isoh2p | 0         | 188      | 4208     | 638       | 1072    |
| Benzo  | 1254      | 0        | 2889     | 137       | 483     |
| Al2O3  | 3930      | 405      | 0        | 1488      | 3041    |
| Salcyl | 1197      | 39       | 2991     | 0         | 449     |
| PABA   | 1052      | 72       | 3198     | 234       | 0       |

[a]The distance between any two compound-cluster combinations is given in terms of the column-heading compound in the direction of the row-heading compound.
[b]isophthalic acid
[c]benzoic acid
[d]aluminum oxide (the diluent in later tables)
[e]salicylic acid
[f]p-aminobenzoic acid

TABLE II

Distance (in skew-adjusted SDs) of Four Pure Ground (100 mesh) Compounds from a Training Set[a] of Mixtures of Compounds

| Compound           | Distance |
|--------------------|----------|
| Acetylsalicylic acid | 8.20   |
| Dextrose           | 46.33    |
| Whole wheat flour  | 12.71    |
| Sucrose            | 3.88     |

[a]Training set composed of mixtures of benzoic acid, isophthalic acid, salicylic acid, p-aminobenzoic acid, and aluminum oxide diluent.

TABLE III

Distance (in skew-adjusted SDs) of Real and False (contaminated) Mixtures from the Mixture Training Set Used in Table II

| Sample No. | Real Samples[a] (Validation Set) | False Samples[b] (Contaminated Set) | Contaminant (%) |
|------------|----------------------------------|-------------------------------------|-----------------|
| 1          | 1.29                             | 6.59                                | 1.1             |
| 2          | .61                              | 3.25                                | 8.0             |
| 3          | .76                              | 5.05                                | 3.8             |
| 4          | .47                              | 4.55                                | 14.8            |
| 5          | 1.97                             | 2.66                                | 4.2             |
| 6          | 1.54                             | 1.77                                | 19.9            |
| 7          | 1.65                             | 6.53                                | 1.7             |
| 8          | 1.18                             | 3.34                                | 1.0             |
| 9          | .79                              | 3.88                                | 10.7            |
| 10         | 1.10                             | 2.32                                | 4.5             |

(Note: the cluster surface is customarily defined as being three standard deviations from the center of the cluster.)
[a]"Real" mixtures contain benzoic acid, isophthalic acid, salicylic acid, p-aminobenzoic acid, and aluminum oxide; the real samples form a validation set because they contain the same compounds as the training set samples.
[b]"False" mixtures contain the same components as real mixtures and acetylsalicylic acid.

TABLE IV

Distance Response of the BEAST (in skew-adjusted standard deviations) for Two Groups of Similar Contaminant Concentrations in the False Samples for Table III

| Sample No. | Distance (SDs) | Diluent (%) | Acetylsalicylic Acid (%) |
|------------|----------------|-------------|--------------------------|
| 1.         | 6.59           | 67          | 1.1                      |
| 7.         | 6.53           | 64          | 1.7                      |
| 8.         | 3.34           | 50          | 1.0                      |
| 3.         | 5.05           | 57          | 3.8                      |
| 5.         | 2.66           | 41          | 4.2                      |
| 10.        | 2.32           | 44          | 4.5                      |

The invention has been described illustratively, not restrictively, and those of ordinary skill in the art will recognize modifications that are intended to be included within the spirit and scope of the invention that is to be delimited solely by the appended claims.

What is claimed is:

1. A method for analyzing a sample comprising the steps of:
    assembling a first plurality of known samples to provide a training set of known samples;
    sequentially placing each of the training set of known samples in a spectroscopic apparatus for measuring a property of the sample as a function of an observable parameter;
    measuring the property of the known samples to obtain a training set of spectra at a plurality of values of the observable parameters;
    storing said training set of spectra;
    forming a bootstrap distribution from the training set of spectra;
    measuring the property of test samples at the plurality of values of the observable parameters to obtain a set of test spectra;
    storing said test spectra;
    forming a univariate distribution from the bootstrap distribution, the univariate distribution comprising points of the bootstrap distribution located within a predetermined distance of a line between a center point of the bootstrap distribution and the test spectrum of the test sample;
    determining skew-adjusted confidence limits from the bootstrap distribution's center and a median of the training set median and a median of the univariate distribution; and determining whether the test sample is a member of the sample population based on the skew-adjusted confidence limits.

2. The method of claim 1, wherein the points from the bootstrap distribution are located by forming a plurality of planes, each plane connecting the bootstrap distribution's center, a point in the bootstrap distribution, and the test spectrum.

3. The method of claim 1, wherein the skew-adjusted confidence limits are determined by calculating a projected difference between the bootstrap distribution's center and the training set's median projected onto the line, and adjusting the projected difference by a predetermined factor and the univariate distribution's median.

4. The method of claim 1, wherein the spectroscopic apparatus is a mass spectrometer, and the observable parameter is mass.

5. The method of claim 1, wherein the spectroscopic apparatus is a spectrometer, and the observable parameter is wavelength.

6. The method of claim 5, wherein the spectrometer is a near-infrared spectrometer.

7. A method for testing a sample to determine if it is adulterated comprising the steps of:
    assembling a first plurality of known unadulterated samples to provide a training set of known unadulterated samples;
    sequentially placing each of the training set of known unadulterated samples in a spectroscopic apparatus for measuring a property of the sample as a function of an observable parameter;
    measuring the property of the known unadulterated samples to obtain a training set of spectra at a plurality of value of the observable parameters;
    storing said training set of spectra of known unadulterated samples;
    forming a bootstrap distribution from the training set of spectra;
    measuring the property of the test sample at the plurality of value of the observable parameters to obtain a set of test spectra;
    storing said test spectra;
    forming a univariate distribution from the bootstrap distribution, the univariate distribution comprising points of the bootstrap distribution located within a predetermined distance of a line between the center of the bootstrap distribution and the test spectra;
    determining skew-adjusted confidence limits by calculating a projected difference between the bootstrap distribution's center and a median of the training set projected onto the line, and adjusting the projected difference by a predetermined factor and a median of the univariate distribution; and
    determining whether the sample being tested is adulterated based on the skew-adjusted confidence limits.

8. The method of claim 7, wherein the points of the bootstrap distribution are located by forming a plurality of planes, each plane connecting the bootstrap distribution's center, a point in the bootstrap distribution, and the adulterated sample's spectrum.

9. The method of claim 7, wherein the spectroscopic apparatus is a mass spectrometer, and the observable parameter is mass.

10. The method of claim 7, wherein the spectroscopic apparatus is a spectrometer, and the observable parameter is wavelength.

11. The method of claim 10, wherein the spectrometer is a near-infrared spectrometer.

* * * * *